(12) United States Patent
Bernhagen et al.

(10) Patent No.: US 6,511,831 B1
(45) Date of Patent: Jan. 28, 2003

(54) ELECTRICAL INTEGRATED NUCLEIC ACID ISOLATION, PURIFICATION AND DETECTION

(75) Inventors: Jürgen Bernhagen, Tübingen (DE); Herwig Brunner, Stuttgart (DE); Frank Vitzthum, Hildrizhausen (DE); Bentsian Elkine, Stuttgart (DE); Georg Geiger, Pforzheim (DE); Gü nter Tovar, Stuttgart (DE)

(73) Assignee: Fraunhofer-Gesellschaft zur Forderung der Angewandten Forschung E.V. (DE)

( * ) Notice: Subject to any disclaimer, the term of this patent is extended or adjusted under 35 U.S.C. 154(b) by 0 days.

(21) Appl. No.: 09/674,655

(22) PCT Filed: May 4, 1999

(86) PCT No.: PCT/EP99/03047
§ 371 (c)(1),
(2), (4) Date: Dec. 19, 2000

(87) PCT Pub. No.: WO99/57314
PCT Pub. Date: Nov. 11, 1999

(30) Foreign Application Priority Data

May 4, 1998 (DE) ......................... 198 19 889
Feb. 15, 1999 (DE) ......................... 199 06 277

(51) Int. Cl.⁷ .................. C12Q 1/68; C12P 19/34; G01N 33/00; G01N 33/559; C07H 21/04
(52) U.S. Cl. ................. 435/91.1; 435/6; 435/287.2; 436/94; 536/23.1; 536/24.3; 536/24.33; 204/456; 204/461
(58) Field of Search ................. 435/6, 91.1, 287.2, 435/91.2; 436/94; 536/23.1, 24.3, 24.33; 204/456, 461

(56) References Cited

U.S. PATENT DOCUMENTS

| | | | |
|---|---|---|---|
| 5,612,207 A | 3/1997 | Nicolau et al. | 435/173.6 |
| 5,650,489 A | 7/1997 | Lam et al. | 530/334 |
| 5,676,646 A | 10/1997 | Hofmann et al. | 604/4 |
| 5,695,650 A | 12/1997 | Held | 210/748 |
| 5,849,486 A | * 12/1998 | Heller et al. | 435/6 |
| 6,146,511 A | * 11/2000 | Slater et al. | 204/457 |

FOREIGN PATENT DOCUMENTS

| | | |
|---|---|---|
| DE | 29702254 | 7/1997 |
| EP | 0301899 | 2/1989 |
| WO | 86/0515 | 10/1986 |
| WO | 93/22678 | 11/1993 |
| WO | 97/27317 | 7/1997 |

OTHER PUBLICATIONS

*Römpps Chemie–Lexikon*, Dr. Otto–Albrecht Neumüller, Franckh'sche Verlagshandlung Stuttgart, 1972, pp. 638 and 639.

* cited by examiner

Primary Examiner—B. L Sisson
(74) Attorney, Agent, or Firm—Ostrolenk, Faber, Gerb & Soffen, LLP

(57) ABSTRACT

The invention relates to a method and a device for the isolation and purification of nucleic acids. According to the invention, after decomposition of a sample the nucleic acids present in said sample are isolated and purified.

17 Claims, 3 Drawing Sheets

ELECTRICAL INTEGRATED NUCLEIC ACID ISOLATION, PURIFICATION AND DETECTION

DESCRIPTION

Figure 1:
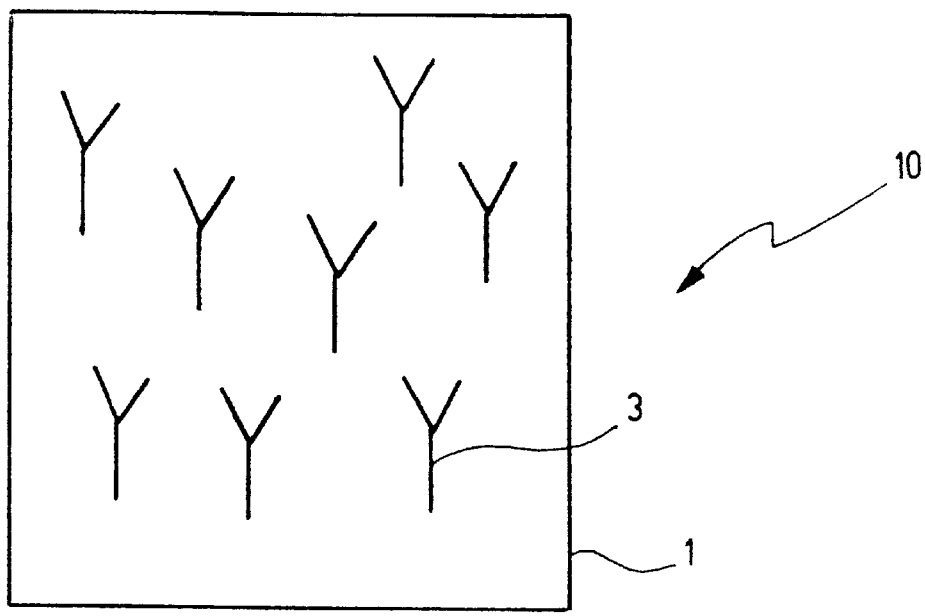

The present invention relates to a procedure and a device for isolating nucleic acids from a sample, in particular a biotic or abiotic material.

The specific or quantitative isolation of nucleic acids from certain source materials plays a great role in a large number of scientific, industrial or other areas. Such areas are for example environmental analysis, forensic technology, basic research, foodstuff diagnosis, veterinary diagnostics, epidemiology, tumour diagnostics, genetic material analysis, analysis of genetic and infectious diseases, monitoring of diseases, therapy of diseases, early detection of multiple-drug resistant germs, soil analysis, research and development of pharmacological substances and vaccines, agro-technology or the like. The source materials for the isolation of the nucleic acids can be as diverse as the application areas, for example eukaryotic or prokaryotic cells or their homogenates, soil samples, blood samples, body fluids or tissue homogenates. Depending on this source or sample material different analysis procedures must be used, for example, in order to make the nucleic acids present in cells and/or cell nuclei accessible for isolation. Treatment by ultrasound and/or enzymes are examples of commonly used dissociation procedures. After carrying out the dissociation treatment, the nucleic acids are isolated for example by way of gel electrophoresis, ultra-centrifugation or affinity chromatography.

In contrast to traditional procedures such as enzyme-immuno-assays (EIA), cell cultures and animal tests, genetic investigations using appropriate nucleic acid diagnostics yield, rather rapidly, more sensitive and more specific results, so that costs can be reduced. Nucleic acids diagnostics is based on the isolation of nucleic acid, that is, the preparation of the sample for releasing nucleic acids from biological material, the purification of nucleic acids, their detection and the subsequent analysis —vide for example Lichtensteiger et al., J. Clin. Microbiol. 34 (1966), 3035 to 3039.

Suitable for deployment in nucleic acid diagnostics, affinity chromatography is based essentially on the capacity of nucleic acids to reversibly bind to positively charged and/or positive-pole matrices. Usually at first an anionic or polar binding of the nucleic acids to the matrix is effected, and subsequently impurities are removed from the nucleic acid by means of suitable solvents. In a second step the nucleic acid bound to the matrix is detached from the matrix by means of a further solvent, for example one having a greater ion density. Subsequently the nucleic acid thus isolated will generally have to be de-ionised so it can be used in further analyses.

It proves disadvantageous in this case that, depending on the sample material and the dissociation procedure used, different strategies for isolation must be developed and deployed. In addition, it is not possible to carry out sample dissociation and nucleic acid isolation respectively purification in a single step.

Both DNA and RNA are commonly also isolated by ultra-centrifugation, in which case protease and phenolic treatments must often be employed. This modus operandi has the disadvantage that in particular DNA of high molecular weight will often remain contaminated with impurities even after the isolation process, and that the molecules are exposed to the danger of breaking up due to the shear forces acting upon them. Furthermore, the phenolic treatment is damaging to health and to the environment.

A further method is based on the binding of nucleic acids to silica materials under high-salt conditions, such as 6M GdnSCN, which would then also have been used earlier as a cell dissociation agent. The use of such materials now proves a disadvantage because of their poisonous nature, viscosity and inhibition effect on subsequent processes such as PCR.

Gel electrophoresis, often used to isolate nucleic acids, also has its disadvantages, among other things due to the required relatively laborious pre- and post-processing of the samples respectively the nucleic acids.

The technical problem on which the present invention is based thus lies in the task of providing a cost-effective and simple procedure for cell dissociation and nucleic acid isolation that permits the. highly specific preparation, from any biotic and/or abiotic sample material, of particularly pure nucleic acids in a single step already during the dissociation of the sample. This procedure is to be capable, in principle, of quantitatively isolating nucleic acids as a class of substances from many single individuals, as well as specifically isolating and purifying quite specific nucleic acid sequences.

The invention solves this problem by providing a procedure for isolating nucleic acids from a sample, with the sample being dissociated under the influence of at least one electric field and the nucleic acids released being brought into contact with a nucleic acid-affine material in such a way that at least part of the nucleic acid binds to the nucleic-acid affine material. The invention in particular relates to an afore-mentioned procedure, with a free respectively uncombined or immobilised nucleic acid-affine material being so brought into contact with the sample, after this has been electrically dissociated, that a combination respectively hybridisation of nucleic acids present in the sample can take place with the nucleic acid-affine material and whereby, as the case may be, the bound nucleic acids can, after a washing step effected as required, be separated from the nuclear acid-affine material and for example be amplified, detected, or otherwise utilised. In this context "affine" can also refer to the. binding of nucleic acids to positively charged materials.

The invention thus provides an affinity chromatography procedure for isolating nucleic acids, whereby the nucleic acids contained in a sample are—after dissociation of the sample by means of at least one electric field—brought into contact with a nucleic acid-affine material and this nucleic acid-affine material binds specific individual, several or all respectively essentially all nucleic acids such as for example DNA or RNA that are contained in the sample and thus isolates them from the other components, of the sample such as proteins, carbohydrates, fats or, as the case may be, nucleic acids that are not of interest. The hybridisation conditions that must be maintained to this end, such as temperature and buffer composition and/or the electrical parameters of the field such as pulse count, pulse frequency or field strength, depend on each concrete isolation task at hand.

The invention thus advantageously provides a single-step procedure, whereby in the course of a single process step a sample is dissociated under the influence of at least one electric field and simultaneously or subsequently the nucleic acids released and originating from the sample are brought into contact with a nucleic acid-affine material in such a way that, depending on the characteristics of the nucleic acid-affine material deployed, either quantitatively all or essentially all nucleic acids or only single nucleic acid groups respectively individual nucleic acid sequences can be separated.

The invention makes possible a universally utilisable nucleic acid diagnostic technology for gene and genome analysis that is capable of being standardised and automated and which has a multitude of application possibilities. The procedure according to the invention is very speedy, with the material effort deployed being low and the use of costly and poisonous substances being minimal. Finally the risk of cross-contamination is reduced, so that the procedure is very sensitive. In addition the procedure can be carried out cost-effectively. The procedure according to the invention furthermore has the advantage of achieving such a high degree of purification of the nucleic acids during nucleic acid isolation and purification that subsequent amplification of nucleic acids is possible without interference from amplification inhibitors and cross-contaminations, which would lead to false-negative or false-positive results. Thus the electric cell dissociation, for example, can take place entirely without addition of chemical dissociation agents, which again could interfere.

In a preferred embodiment of the invention, it is provided for the sample to be subjected to the influence of at least one electric field of constant voltage or a pulsed electric field for releasing the nucleic acids and/or the lysis of the biological sample. Under the influence of the electric field and the electric penetration pores are created in the lipid layers making up the cell membrane. As part of the use of pulsed electric fields one can combine an electroporation and an osmotic lysis of cells, so that the nucleic acids present in the sample are completely released and can also be purified. Suitable parameters for pulsed electric fields are found for example in Kinosita and Tsong, Nature 268 (1977) 438 to 441; Proc. Natl. Acad. Sci. USA 74 (1977), 1923 to 1927 or Benz and Zimmermann, Bioelectrochem. Bioenerg. 7 (1988), 723 to 739, which are to that extent included in the present disclosure content. It must be pointed out here, however, that the presently described procedure does not concern electroporation, which is know, but the reverse process of nucleic acid exit. According to the invention, field strengths from 0.5 to 50, preferably from 5 to 30 kV/cm and pulse lengths respectively time constants of about 0.5µs to 50 ms as well as 1 to 1 000 000 pulses, preferably 1000 to 10 000 pulses, may be employed. Of course electrical parameters that differ considerably from these may also be used. For example the pulse form may be rectangular, decrease exponentially or sinus-shaped, preferably in the region of radio frequency. The electric field may be created in this case either by alternating voltage or by direct voltage. Common electrical parameters are described also in, for example, U.S. Pat. Nos. 5447,733; 5,235,905 or U.S. Pat. No. 5,393,541, which to that extent are included in the disclosure content of the present invention. The field strengths to be employed preferably lie above the critical voltage $V_c$ above the membrane of the biological material. Further suitable conditions are described, for example, in Vitztum et al., FEBS Abstracts, 155 (1998), which to that extent is included in the disclosure content. By means of the use of pulsed electric fields for the isolation of nucleic acids it is possible, for example, according to the invention, to achieve the lysis of only certain cell types in a suspension, ie. the sample used, by way of choosing the treatment parameters. Thus certain nucleic acids of one cell type can be separated from the nucleic acids of another cell type. In addition one can achieve a selective release of nucleic acids from the cells of one cell type amid use of pulsed electric fields by the choice of suitable conditions, whereby the resulting chromatographic effects leads to a combination of a nucleic acid isolation and a nucleic acid purification.

In a further form of embodiment of the invention, an electric field of constant voltage is used for cell dissociation under conditions described for example in Pollard-Knight et al. WO 97/41219 (1997), which to that extent is included in the present disclosure content.

During the dissociation of the sample it is also possible to introduce, by means of the electric fields, substances into the cells or micelles which later promote the lysis and/or nucleic acid release, specify these or serve as markers for a subsequent detection.

Of course it is also preferred, according to the invention, to cause several equal or different electric fields to act upon the sample simultaneously or sequentially.

It is also preferred, according to the invention, to promote cell dissociation by the use of high temperatures, for example from 30°C. to 95° C.

Obviously, it is also possible to carry out sample dissociation with other parameters of the electric field and/or to provide for adding chemical agents, as the case may be, such as chaotropic substances or detergents, agents that promote cell dissociation, for example SDS, lipases, proteases such as protease K or DMSO (dimethylsulfoxide), urea, guanidinium thiocyanate or guanidinium hydrochloride.

It is preferred, however, to carry out the process according to the invention without the addition of chemical substances, for example exclusively in water, physiological salt solution or buffer solution.

This is because it is in fact an essential advantage of the present invention that no chaotropic reagents or detergents need be used for cell dissociation, but that the cell dissociation can be carried out in physiological solution, buffer solution or water.

In a particularly advantageous manner one can provide for the sample—having been brought into contact with the immobilised or free nucleic acid-affine material—to be subjected to the. influence of ultrasound in combination with the electrical treatment, for example by way of electrical spark discharge, as described in U.S. Pat. No. 5,368,724, so as to promote sample dissociation, in particular cell dissociation. This at the same time results in a rise in temperature of the reaction mix of sample and nucleic acid-affine material, so that the DNA contained in the sample is denatured and can bind to the immobilised DNA mixture as it cools. In addition, a potentially advantageous fragmentation of the nucleic acid occurs. The ultrasound effect thus promotes the dissociation of the sample and/or the binding of the nucleic acids to the nucleic acid-affine material.

According to the invention, it is preferably provided for not only the cell dissociation but also the binding of the released nucleic acids to the freely present or immobilised nucleic acid-affine material amid application of an electric field.

In a further preferred embodiment of the invention it is provided for at least one electric field, for example one or more pulsed electric fields and/or one or more fields of constant voltage, to be applied during the bringing into contact of the released nucleic acids with the nucleic acid-affine material so as to effect an electrohybridisation. The electro-hybridisation favours the hybridisation respectively binding or adsorption of the nucleic acids to the nucleic acid-affine material and may improve the specificity of the bond. It may be provided, according to the invention, for concentrating the released, electrically negatively charged nucleic acids amid application of a voltage initially in the area of the anode of a sample chamber employed for carrying out the procedure, whereby one may, for instance, advantageously provide for immobilised nucleic acid-affine material to be present in the anode area, so that there results a locally high concentration of nucleic acid in the area of this nucleic acid-affine material that kinetically and thermodynamically favours an adsorption respectively hybridisation. According to the invention one may provide for a pole reversal of the electric field during the bringing into contact of the nucleic acids with the nucleic acid-affine material, so that due to the changed kinetic and thermodynamic conditions electro-stringent washing can take place in the cathode area.

If free nucleic acid-affine materials, for example uncombined random sequences, are employed, the electrophoretic effects that occur during the migration of the negatively charged nucleic acids with the preferably equally negatively charged nucleic acid-affine material can be exploited while an electric field of constant voltage or a pulsed electric field is applied in the course of the electro-hybridisation provided according to the invention.

If the nucleic acid-affine material is thus freely present, according to the invention, during sample dissociation it must preferably possess a negative net charge in order to promote the purification of nucleic acid by way of electrophoretic effects. In the electric field, preferably a non-homogenous electric field, the nucleic acid-affine and the released nucleic acids travel in the same direction toward the anode, so that their concentration locally increases there. Besides the separation of substances with other electrical characteristics this has the advantage of promoting the association of nucleic acid-affine material and nucleic acid.

If the nucleic acid-affine material present is immobilised, for example bound to the sample carrier, according to the invention electro-hybridisation can be carried out. In addition, electro-stringent washing and electro-elution can be carried out during or after electro-hybridisation, as described for example in Hintsche, Medizinische Genetik 11 (1999), 12 to 13; Cheng et al., Anal. Chem. 70, (1998), 2321 to 2326; Cheng et al., Nat. Biotechnol. 16 (1998), 541 to 546; DE 196 28 171 and U.S. Pat. No. 5,632,957, which to this extent are included in the disclosure content of the present invention. Obviously electro-stringent washing and electro-elution may also be provided when free, nucleic acid-affine material is employed, as the case may be.

The invention thus provides for, in a preferred form of embodiment, the application of one or more electric fields that may be pole-reversed as the case may be, during the sample dissociation as well as the simultaneous or subsequently occurring bringing into contact of the nucleic acid-affine material with the nucleic acids in order to thereby make possible a release of the nucleic acids and a selective binding of the nucleic acids to the nucleic acid-affine material. By the use of the electric field there may also occur washing of the bound nucleic acids, as the case may be. In a further preferred embodiment it is provided for the subsequent detection step of the purified nucleic acids also to take place by electric detection by means of an electric field. Hereby one may proceed as described in Hintsche, Medizinische Genetik 11 (1999), 12–13. But the detection may also be carried out by means of traditional optical, spectrophotometric, luminometric or radioactive manners of procedure.

The nucleic acid-affine materials may be present either freely in solution or immobilised at a matrix, for example a sample carrier or even the electrodes themselves. An electrode or a wall area of a sample chamber made from non-conducting material may also serve as matrix.

The invention provides, in another preferred embodiment, for the remainder of the sample, following binding of the nucleic acids to the nucleic acid-affine material, to be separated from the nucleic acids bound to the nucleic acid-affine material, and for the isolated nucleic acids, in a preferred form of embodiment, to be washed, for example also under the influence of an electric field, that is, electro-stringent washing is carried out.

In a further preferred embodiment, the invention provides for detection to be carried out, following binding of the nucleic acids to the nucleic acid-affine material, before or after separation of the remainder of the probe—after preceding amplification, as the case may be—of the bound nucleic acid, for example by means of PCR, in particular optically for instance luminometrically or spectrophotometrically, radioactively or electrically.

In a particularly preferred embodiment it is possible to carry out dissociation of the sample, sample purification and detection in a single-step process in one and the same sample carrier, with preferably an electric field being applied respectively connected at certain times which assures sample dissociation, nucleic acid purification and detection. Any amplification of the nucleic acids to be detected that may be carried out, as the case may be, may, according to the invention, be an electric isothermic amplification, as it is described in WO 98/02573, WO 93/15224 or WO 95/25177, which are to that extent included in the present disclosure content.

The invention thus makes available a procedure by which the isolation of nucleic acid from a sample, the purification of nucleic acid by binding to nucleic acid-affine material, as the case may be, washing of the isolated nucleic acids and their detection, can be carried out in a one-step process under the influence of at least one electric field. The integration so achieved makes possible the basis for a product, that is, a device, by means of which all above-mentioned steps may be carried out in a single step in one sample chamber, that is, nucleic acid diagnostics are considerably sped up, the threat of cross-contaminations is reduced, sensitivity and specificity are increased as well as automation, also in chip form factor, that is, the millimetre region, becomes possible.

In the context of the present invention the term sample is understood to mean any organic, inorganic or biotic/abiotic material whatsoever, as long as it contains a nucleic acid, in other words DNA or RNA. A sample may thus be a prokaryotid or eukaryotid cell or a cell homogenate, a virus, for example contained in the form of a virus suspension, blood, sperm, lymph or other body fluid, organ or tissue preparation, water or soil samples, liposomes, cellular organelles, cell nucleus, yeast, plant homogenates, amber or other. The sample preferably contains water or a physiological salt- or buffer solution as solvent means.

In the context of the present invention the words sample dissociation is taken to mean as complete as possible a release of nucleic acids, respectively, as the case may be, the release of nucleic acids by selected sequence and/or compartment, from a biological material, thus a sample, and which may be accompanied by a destruction of the sample, e.g. lysis, or reversible damage to the sample, for example pore formation.

In the context of the present invention the term nucleic acid-affine material is taken to mean a material that is capable of binding, preferably reversibly, nucleic acids. In a preferred embodiment of the invention, the nucleic acid-affine material is a material that binds, non-specifically with regard to the actual nucleic acid sequence, all or essentially all nucleic acids in a sample, for example silica, diatoms, or anionic exchangers. DNA mixtures consisting solely of random sequences, proteins, carbohydrates, glycoproteins, or proteoglycanes are also materials that bind nucleic acids quantitatively, and thus are nucleic acid-affine materials within the meaning of the invention. Of course the term nucleic acid-affine material is also understood to mean material that binds only certain nucleic acids, that is, which possesses nucleic acid specificity, such as for instance fragmented target genomes. But nucleic acid-affine material also refers to a most highly sequence-specific nucleic acid which quite specifically only isolates and binds a specific nucleic acid species from a sample containing many nucleic acid species, for example a certain cDNA or genomic DNA sequence. In the preferred embodiment of the invention the nucleic acid-affine materials are for example random oligonucleotides or sequence-specific oligonucleotides having for example a length of 7 to 50 nucleotides.

In the context of the present invention the term DNA mixture consisting solely of random sequences is taken to mean a mixture of random DNA sequences that are also described as random primers and which is not specifically tailored to any specific nucleic acid that is to be isolated, but instead possesses any permutation of nucleotides whatsoever, so that without distinction all nucleic acids present in the sample having a sufficiently great chain length for hybridisation, are bound. The random DNA sequences possess an essentially uniform but random chain length, preferably an average chain length of 15 to 30. The DNA mixture consisting solely of random sequences thus possesses a multitude of different DNA molecules in the form of single strands, whose sequence is in each case composed at random.

To prepare this DNA mixture one proceeds in such a way that during the course of the DNA synthesis the four nucleosides involved in the construction of DNA, ie. deoxyadenosine, deoxyguanosine, deoxycytidine and deoxy-thymidine, as well as, as the case may be, their respective synthons, that is, their structurally analogue modifications, are deployed in a mixing ratio of 1:1:1:1 per chain elongation step. As a consequence, for each position all four nucleosides have the same chance of being built into the DNA molecule chain. A DNA mixture having random DNA sequences of for example 20 nucleotides length each, represented by the sequence 5' $(N)_{20}$ 3', where N stands for deoxyadenosine, deoxyguanosine, deoxythymidine, and deoxycytidine, therefore represents a mixture of all single-strand DNA molecules having a chain length of 20 nucleotides, i.e. $4^{20}$ different DNA molecules. The number of distinct random DNA sequences per DNA mixture according to the invention thus is $4^x$, with x being the chain length or number of nucleotides of the random DNA sequence.

In a particularly advantageous embodiment of the invention, the invention relates to an afore-mentioned procedure in which the $4^x$ random sequences present in the DNA mixture occur in equal, preferably essentially molar quantities. The DNA mixture deployed according to the invention has thus not been developed with a view to a specific isolation task, but constitutes, on the contrary, a DNA mixture without any concrete specificity for DNA or RNA capable of being used for any desired task of isolating DNA or RNA. The DNA mixture deployed is specific only insofar as it is capable of separating nucleic acids, i.e. DNA or RNA, from other materials such as proteins, sugars or the like. But one can provide, according to the invention, for distinguishing between DNA and RNA by suitable selection of binding respectively hybridisation conditions between nucleic acid to be isolated and nucleic acid-affine material, or of the solution conditions (temperature, ion density etc.). The procedure according to the invention can thus be carried out, in an advantageous manner, specifically for DNA or RNA.

Of course the DNA mixture of random sequences or specific oligonucleotides to be deployed according to the invention may also contain other nucleosides such as deoxyinosine, uridine, pseudo-uridine, $N^2$-dimethyl-guanosine, $N^6$-isopentenyladenosine, ie. synthons. According to the invention, one can also provide for deploying pentoses, that is, RNA building blocks, instead of the deoxypentoses. In the context of the present invention the term DNA mixture may thus also be read as RNA mixture, as the case may be.

According to the invention oligonucleotides in particular may be employed as nucleic acid-affine material, whereby highly specific probes as well as more non-specific oligonucleotides such as fragmented target genomes or random oligonucleotides, ie. DNA mixtures consisting solely of random sequences, so-called random oligonucleotides, may be employed. The use of random oligonucleotides as the nucleic acid-affine material has the advantage, compared to materials such as anion exchangers and silica, which can also be used according to the invention, of a lesser affinity vis-à-vis other poly-anions than nucleic acids and a higher affinity for the nucleic acids due to the principle of complementary base pairing compared to materials such as silica or anion exchangers, but compared with oligonucleotides with specific sequences they are suitable for the purification of various different nucleic acids. Coupling of the oligonucleotides to the carrier or the matrix takes place, preferably, via the 3'-end of the oligonucleotide so that during a subsequent amplification, as the case may be, for example by means of PCR, no by-products can occur. When specific oligonucleotides are employed it is preferable, according to the invention, to use melting temperatures below those of the PCR primers so as to minimise competition.

Besides the preferred use of DNA oligonucleotides the use of RNA nucleotides and peptide nucleic acids (PNAs) is possible according to the invention. Furthermore it is preferred according to the invention to employ modified bases in order to achieve certain hybridisation effects. The use of specific sugars in connection with nucleic acid oligonucleotides, too, as described in Beier et al., Science 283 (1999), 699 to 703, is provided according to the invention and thus far included in the present disclosure content.

The invention possesses the advantage that from one sample one can, in a single step even during the sample dissociation, isolate and obtain in pure form highly specifically nucleic acids, so that these can directly be used for other analysis or preparation steps, such as for example a PCR process. The procedure according to the invention advantageously does not presuppose any costly or time-intensive steps to adapt the procedure for each respective isolation task. Rather, the procedure according to the invention can be used directly, without further modification, for any desired isolation task.

In a particularly preferred form of embodiment of the invention, it is provided, after affinity binding of the nucleic acids present in the sample to the nucleic acid-affine material, for impurities to be removed by means of suitable buffer solutions or water. Following the washing step the affinity-bound nucleic acid may be separated from the nucleic acid-affine material by means of increasing the ambient temperature, for example to at least 70° C., for example simmering temperature, in the presence of a suitable solvent, for instance a buffer solution or water. The separation may also be carried out by increasing the ion density of the solvent buffer or a change in the pH value or by electric washing. The resulting nucleic acid is free from impurities and can be amplified in particular by PCR processes, including in the presence of the DNA mixture that has been immobilised, as the case may be.

The invention relates, in a further form of embodiment, to an device for isolating and processing nucleic acids, in particular for carrying out an aforementioned procedure, with the device, subsequently also designated sample carrier, possessing at least a sample chamber with at least two planar-shaped electrodes and at least one non-conducting frame part, and with the at least two planar-shaped electrodes and the at least one frame part being formed as wall, lid or bottom part. The sample chamber according to the invention thus possesses a chamber having a circular or rectangular cross-section enclosed by bottom part, wall part or parts, and as the case may be, lid part, with regions of the wall, bottom and/or lid parts are formed as planar-shaped electrodes. The at least two electrodes provided according to the invention, disposed preferably opposite each other, possess electrical connections and serve for the creation of an electric field of constant voltage or a pulsed electric field for enabling sample dissociation and, as the case may be, electro-hybridisation, electric washing and electro-elution as well as electro-detection. Preferably, the at least one non-conducting frame part possesses at least one opening, for example insertion and withdrawal units, which serve to introduce or remove sample liquid. In addition, measuring units may be provisioned, located between areas of the frame part and/or between the electrodes, for example optical measuring units and their connectors, as required, which permit the detection of bound nucleic acids.

In a preferred form of embodiment of the invention, it is provided for the electrodes to consist of aluminium, stainless steel, silver, gold, platinum, graphite or the like, whereas in a further preferred embodiment the non-conducting frame parts are made from plastic, glass, silicium or similar.

The invention thus provides for a sample carrier in which the entire single-step procedure according to the invention can be carried out, that is, the dissociation of the sample, the isolation of nucleic acid, the purification of nucleic acid and, as the case may be, the detection of nucleic acid. It proves advantageous here that the sample liquid need not be transferred among various containers, but that the procedure instead can be carried out in a single container, which is capable of creating an electric field in its interior volume which serves to dissociate the sample and to promote the binding of the nucleic acid to the nucleic acid-affine material. In a particularly preferred manner, the sample carrier is constructed in micro-system technology in the form factor of a chip, thus possessing measurements between 1 cm$^2$ and 2 cm$^2$. The frame part may in such a form of embodiment accordingly be made planar, that is, level, without a sample chamber being provided and with the electrodes present being integrated into the frame part. In this way the amount of material used is minimised and the throughput of samples maximised. Furthermore, using the device according to the invention in chip size brings with it advantages in relation to the voltage to be applied, since due to the small electrode distance high field strength can be reached already at low voltages. Advantageously, the geometry of the sample carrier is to be chosen such that, as the case may be, homogenous as well as non-homogenous electric fields may be created. In a preferred form of embodiment such a chip is built according to the principles of micro-fluidics.

Advantageously the said device according to the invention is characterised in that at least parts of the region of the electrodes and/or the frame part that face toward the interior volume possess immobilised nucleic acid-affine material. Accordingly, an area of the electrodes may for example be linked to specific or non-specific oligonucleotides in a preferred manner according to the invention.

The present invention also relates to a device, in particular an affinity matrix, for isolating the nucleic acids from a sample, in particular for carrying out an afore-mentioned procedure, comprising of a nucleic acid-affine material, for example a DNA mixture consisting solely of random sequences, described above, which is immobilised at a matrix, for instance an electrode. The invention thus provides for a device, in particular an affinity matrix, by means of which the afore-mentioned procedure can be carried out, in particular by means of which nucleic acids can be isolated in a simple and cost-effective manner from any desired sample.

The device according to the invention includes a matrix which may be executed for example as a membrane, as beads, or as columnar gel and which functions as the carrier or basic framework for the DNA mixture consisting solely of random sequences. One may also provide for magnetic particles, for example beads, or electrodes, for example made of aluminium, silver, stainless steel, gold, platinum and/or graphite, to be used as matrix.

The invention provides, in an advantageous manner, for employing a chemically and physically largely inert material for the matrix, for example glass or plastic such as polystyrene, or polypropylene, or an correspondingly inert electrode material.

In particular the material must, in the preferred form of embodiment of the invention, be capable of tolerating temperature differences in a range of 10° C. and 95° C., pH differences ranging from 0 to 14, and sodium—respectively potassium chloride ion concentrations from 10 mM to 2 M without significant change in material characteristics. Furthermore, the material used must preferably be insoluble in water, detergents, and tensides mixtures, as well as chemically inert vis-à-vis chaotropic reagents such as for example isoguanidine thiocyanate.

Advantageously, the matrix is modified on its surface, for example by deposition of bio-molecules that bind to the surface of the matrix material with high affinity. Such a bio-molecule immobilised on the matrix may for instance be streptavidin. The matrix surface may however also be modified in such a way as to make possible a co-valent binding between the nucleic acid-affine material, for example the random sequences of the DNA mixture, and the matrix. Accordingly, the matrix may possess amino groups that can bind to, for example, an amino function introduced at the 5'-end or 3'-end of the random DNA sequences, via a dialdehyde spacer respectively a dialdehyde link molecule, for example glutardialdehyde, amid formation of a Schiff's base. According to the invention one may provide for cleansing the matrix before modification of its surface, for example with nitric acid. Additionally, the invention provides, in a preferred form of embodiment, for the silanisation of the matrix surface prior to modification.

The nucleic acids used as nucleic acid-affine material of the present invention, for example the random sequences of the DNA mixture, accordingly also possess modifications at the 3'-end or 5'-end for the purpose of immobilisation at the matrix. Such modifications may for example be biomolecules linked to the 5' end of the random DNA sequence such as biotin that bind with high affinity to other biomolecules immobilised on the matrix, such as for example streptavidin. One may also provide for introducing amino functions, epoxy groups or succinimide esters, or other common functional groups, into the nucleic acids employed as nucleic acid-affine material, preferably at the 5'-end or 3'-end, so that these can covalently bond, amid formation of a Schiff's base, with aldehyde groups immobilised at the matrix.

In any case the modified nucleic acids, for example the random DNA sequences in single-strand form, and the modified matrix are brought into contact with each other in such a way that the nucleic acids are immobilised at the matrix. The matrix charged with the nucleic acid-affine material in the form of nucleic acids to be employed according to the invention is also termed, in the context of the present invention, an affinity matrix.

The affinity matrix according to the invention may advantageously also be deposited on the surface of particles that are added respectively exposed to the disintegrated material in the course of the dissociation.

The invention also relates to the use of a DNA mixture consisting solely of random sequences, in particular a mixture of equal parts, of $4^x$ different random DNA sequences, with x being equal to the chain length of the random DNA sequence, preferably 5 to 50, in particular 15 to 30, for isolating nucleic acids from a sample.

Further advantageous embodiments become clear from the sub-claims.

The invention is explained in more detail using examples of embodiment and the corresponding figures.

Figure 2:
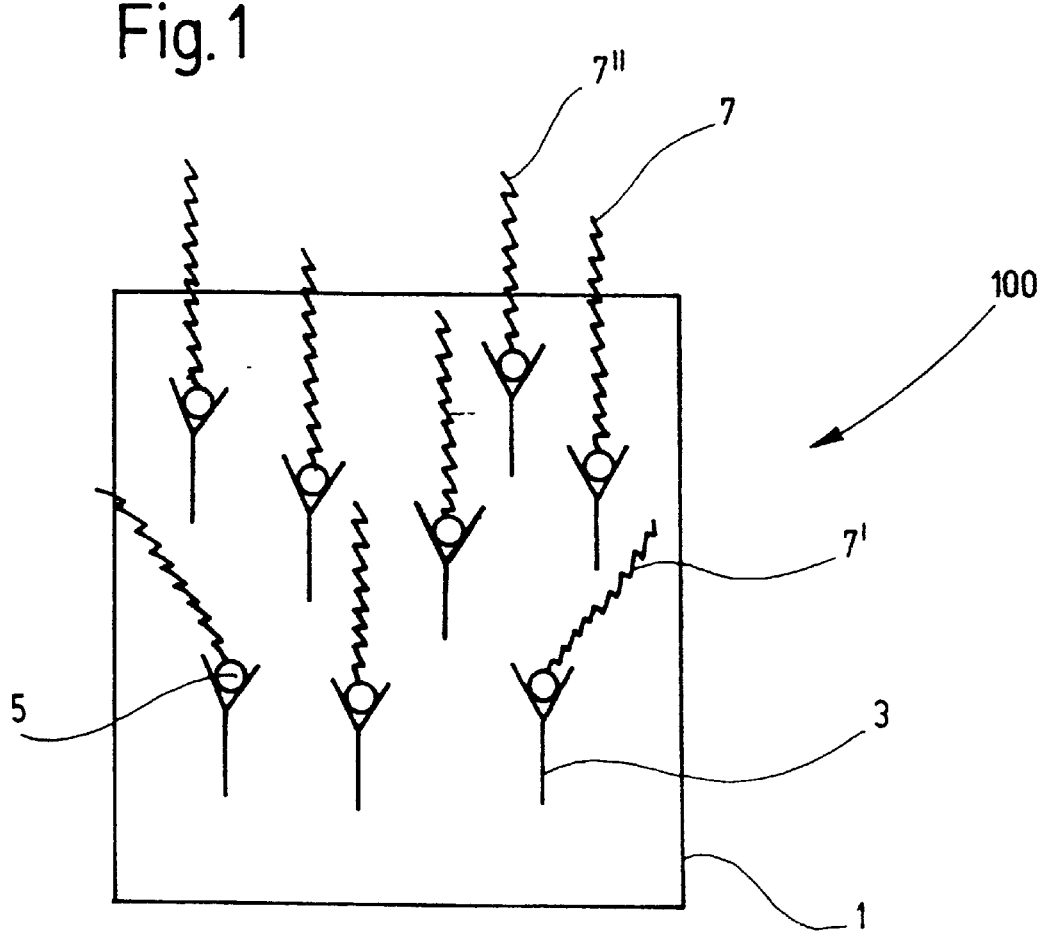
Figure 3:
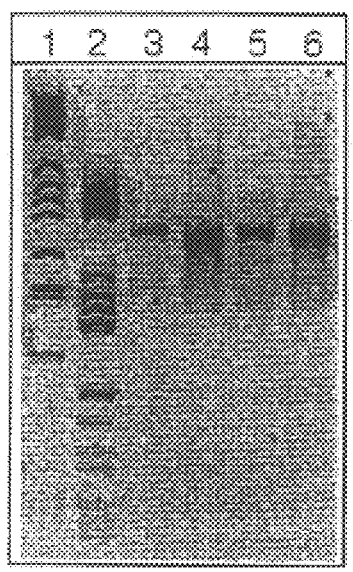
Figure 4:
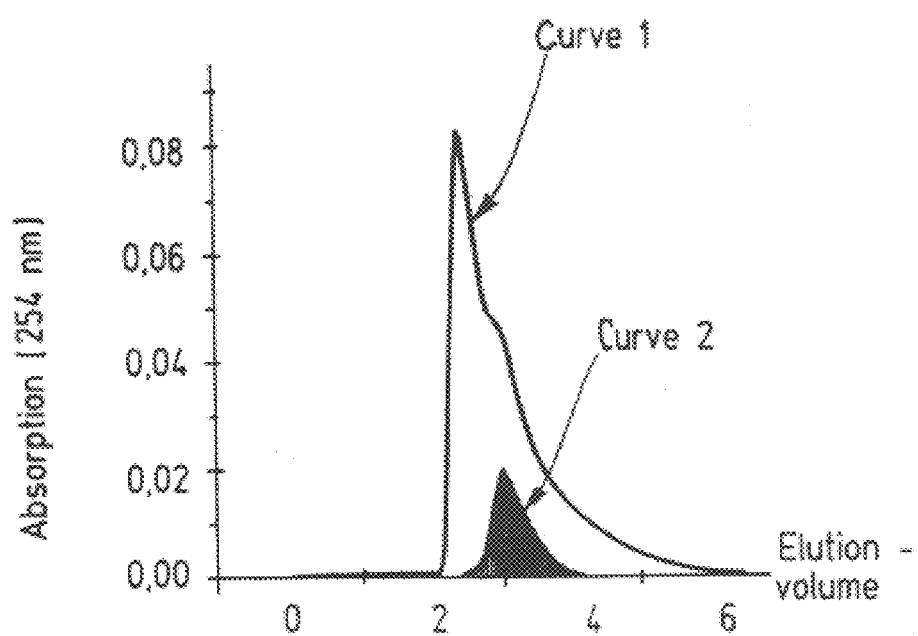
Figure 5:
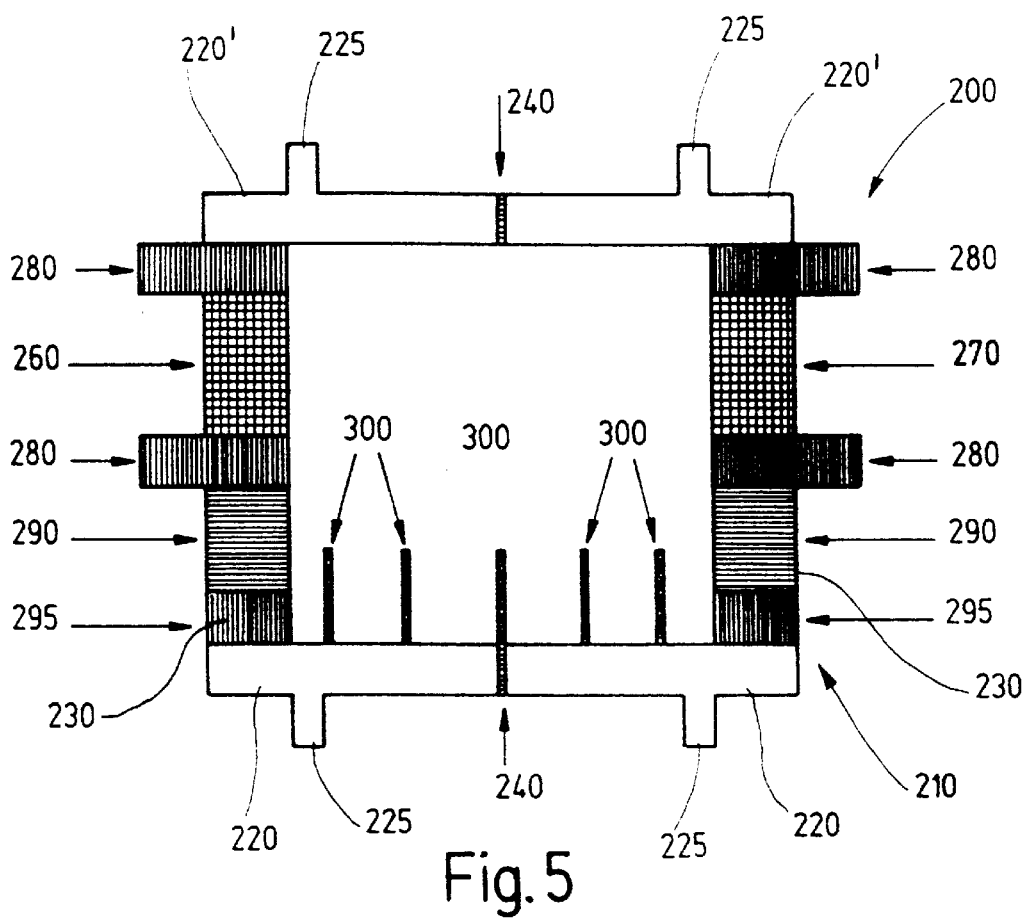
Figure 6:
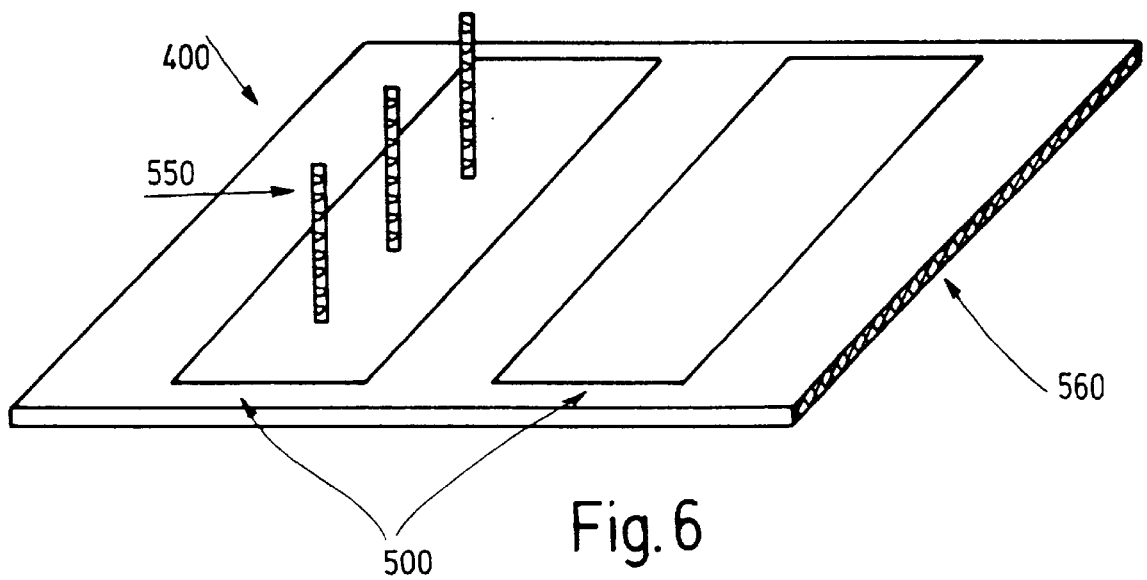

The figures show:

FIG. 1 a matrix of a device according to the invention;

FIG. 2 a device according to the invention, respectively DNA affinity matrix;

FIG. 3 an electrophorograph;

FIG. 4 two chromatographs of the binding of standard DNA to untreated and treated glass beads;

FIG. 5 a further embodiment of a device according to the invention in the form of a sample carrier; and FIG. 6 a further embodiment of a device according to the invention executed as a chip.

EXAMPLE 1

Device for Isolating DNA

FIG. 1 shows a matrix 10, executed in the form of a membrane 1. The membrane 1 is coated on its surface with streptavidin molecules 3.

FIG. 2 shows an affinity matrix 100 that was created by bringing the matrix 10 into contact with 5' modified chemically or synthetically produced random DNA sequences 7, 7', 7" of a DNA mixture in single-strand form, whereby the 5' modification of the random DNA sequence enables the latter to bind with high affinity to the streptavidin molecules 3. FIG. 2 shows that the 5' ends of the random DNA sequence 7, 7', 7" are each bound to biotin 5. The biotin modification at the 5' end of the random DNA sequence 7, 7', 7" binds with high affinity to the immobilised streptavidin molecules 3, so that a DNA mixture having the individual random DNA sequences 7, 7', 7" is formed immobilised on a matrix 10.

EXAMPLE 2

Isolation of DNA from a Cell Dissociation

Creation of the Affinity Matrix

Used for the trials were Ballotini Micro Glass Spheres Type 3000 from the firm Potters-Ballotini GmbH of Kirchheimbolanden. Their size was listed as being up to 50 $\mu$m. The glass beads were boiled in nitric acid in order to clean the basic material and to prepare the surface for silanisation. 50 g of the glass beads were placed in a one-litre three-necked flask with reflux cooler containing 500 mL of about 7% nitric acid. They were heated to boiling point over a mushroom heater and boiled under reflux for 1 hour amid agitation by means of a magnetic stirrer with stirring fish. After cooling the overlaying liquid was decanted. The glass beads were washed three times in water of MilliQ quality and filtered off via a suction strainer. They were dried overnight at 95° C. in a dryer cabinet. Since impurities remained visible to the naked eye after drying, the entire cleaning process was repeated once more.

10 g of the dried and cleaned glass beads were placed in a 250 mL single-neck round flask with 200 mL dry methanol. The flask was flushed with argon. 20 mL of 3-aminopropyltrimethoxysilane (Fluka) were added. 0.5 mL triethylamine were added as a catalyst. The preparation was stirred at room temperature for 2 h. The reaction solution was decanted off and the glass beads washed with water (MilliQ) and filtered off via a suction strainer.

A potassium phosphate buffer was initially made from 160 mL 0.1 M $K_2HPO_4$ and 40 mL 0.1 M $KH_2PO_4$ and stabilised at a pH of 7.5. A 2.5% glutardialdehyde solution was prepared from 10 mL of 25% glutardialdehyde solution and 90 mL of the potassium phosphate buffer. To 40 mL of the 2.5% glutardialdehyde solution 4 g of the silanised glass beads were added and stirred for about 1 h at room temperature. The glass beads were then washed with water, potassium phosphate buffer and once more well washed with water.

Oligonucleotides (1 $\mu$mol per preparation) (15 mers, each 15 mer at the same concentration, ie. there is a distribution of all theoretically possible oligomers with the nucleotides A,T, G and C of equal parts each, firm Interactiva, Ulm, Germany) were absorbed in 1 mL potassium phosphate buffer. In a 15 mL vial (Greiner GmbH) 1 g of the silanised glass beads activated with glutardialdehyde as well as 1 mL of the primer solution were added to 4 mL potassium phosphate buffer. The preparation was briefly cooled in ice. The vial was placed on a roller in a cool room overnight and rolled there for 17 h. The glass beads were centrifuged off in a minifuge (Heraeus) for 5 minutes at 1500 rpm. The excess was decanted off and initially kept in the refrigerator. The pellet was absorbed three times in about 6 mL potassium phosphate buffer and centrifuged off, so as to wash out unbound primer. The beads were turned into a slurry with water (MilliQ) and half each placed in two Eppendorf caps. One half was frozen in this form, the other half was dried in the speed-vac in three passes of 10 minutes each and also stored in the freezer. In order to be able to estimate whether primer had in fact been bound, ultraviolet spectra were taken at 260 mm of the primer source solution and the surplus after binding. From the spectra each respective primer concentration was determined.

B) Cell Dissociation and Isolation of DNA

In a reaction vessel 300 µL of a physiological buffered salt solution (pH7.4; 3 mM EDTA) with $10^9$ KBE/mL of *Escherichia coli* was treated with 100 000 electrical pulses with a field strength of 1.5 kV/cm. The time constant was 2 µs (exponentially decreasing pulse form). The pulse frequency was 5 Hz. Subsequently 50 mg to 500 mg of the affinity beads coated with oligonucleotides were added. The temperature of the reaction mix increased thereby, which was sufficient to denature the double-strand DNA released so that it was able to bind to the affinity matrix by way of hybridisation while the reaction mix cooled. By underlaying the reaction mix with chloroform a phase separation was obtained, with the glass beads concentrating in the chloroform phase due to their high specific weight. The watery overlay, which contains, apart from cell fragments, all water-soluble components of the cell dissociation, was taken off and the glass beads, to which the DNA to be isolated adhered, were dried in a vacuum.

If the isolation of the DNA was carried out on Dynabeads, 50 µL cell lysate was placed in a buffer of the composition 20 mM Tris/HCl pH7.5, 1 M LiCl, 2 mM EDTA, with 50 µL of conjugated Dynabeads having a concentration of 5 mg/mL. The resulting mixture then incubated here for 10 minutes on a roller and for another 10 minutes left standing. The particles charged with DNA were magnetically separated and washed twice according to the manufacturer's recommendation with 100 µL washing buffer each.

C) Elution of DNA from the Affinity Matrix

The affinity matrices containing DNA were warmed either in water or in a buffer of 10 mM Tris, 1 mM EDTA, pH8.0, as desired. The resulting suspension was heated for 10 minutes to boiling point, whereby the DNA bound to the affinity matrix became detached so that it could be removed with the overlay while hot.

EXAMPLE 3

Isolation of DNA and PCR

In a first experiment the feasibility, in principle, of isolating DNA on immobilised random DNA sequences (15 mers, as shown in example 2), was demonstrated. For this purpose, random DNA sequences biotinylated at the 5'-end were immobilised onto commercially available magnetic particles coated with streptavidin and their DNA-binding characteristics compared with the binding characteristics of a commercially available DNA isolation system (DYNAL Direct). A plasmid containing the MIF gene that is released by the chemical dissociation of intact Escherichia coli cells served as reference DNA. Following isolation of the plasmid the MIF gene was amplified with a suitable pair of probes and the PCR products were separated electrophoretically. The results of these comparative tests are shown in FIG. 3. The traces 3 and 4 of the electrophorograph represent the MIF-PCR product of plasmid DNA which could be isolated on random DNA sequences. This is contrasted in traces 5 and 6 by the MIF-PCR products of the plasmid DNA isolated by means of the commercial system. Neither a qualitative nor a quantitative difference between the two strategies for isolation can be shown.

EXAMPLE 4

Affinity Chromatography

The glass beads prepared according to example 2 as an affinity matrix for isolating DNA were transferred to an HPLC column void and tested there as to their capacity to bind DNA. Columnar chromatography procedures have an essential advantage over so-called batch processes in that they are highly reproducible and that one can vary the test conditions (flow rate, flowing agent, temperature) in a simple manner. FIG. 4 shows chromatographs of the binding of standard DNA (25 µg each) at 50° C. and a buffer having the composition 10 mM Tris, 1 mM EDTA, 100 mM NaCl, pH8.0 with untreated glass beads and with glass beads possessing immobilised random DNA sequences. The difference of the areas under the curves (curve 1: glass beads without random DNA sequence; curve 2m: glass beads with random DNA sequence) corresponds to the DNA-binding capacity of the affinity matrix. The flow rate in each case was 0.1 mL/min. Under the conditions chosen it was shown (cf. FIG. 4) that the DNA-binding capacity of the glass beads coated with random DNA sequences was 7.16 times superior to the binding capacity of untreated glass beads.

EXAMPLE 5

Isolation of Nucleic Acid Amid Use of Electric Fields by Means of a Sample Carrier in Chip Form Factor FIG. 5 shows an device 200, comprising a sample chamber 210 made up of four electrodes bundled in two opposite electrode pairs 220, 220' and a frame part 230 made of non-conducting materials. The sample carrier is rectangular in cross-section and built to chip form factor, ie. is of a size of about 1 to 2 $cm^2$. Not shown are the lid and bottom part of the sample chamber 210. Frame part 230 and the four planar-shaped electrodes 220, 220' form the walls and delimit an interior volume that serves to take up the sample. The two opposite electrode pairs 220, 220' that each form one wall may be disposed at a distance of 100 nm to 5 mm and to possess an electrode diameter of about 1 cm. It is shown that non-conducting areas 240 separate the individual electrodes 220, 220' of the respective electrode pairs with their connections 225, so that non-homogenous and approximately homogenous electric fields can be created. Thus the formation of non-homogenous fields can be obtained by feeding a voltage to only two or three of four conducting. elements 220, 220'. Preferably, the non-conducting regions 240 between the conducting elements 220, 220' of an electrode pair are made as small as possible, so that approximately homogenous electric fields can occur when for example the conducting elements, i.e. electrodes, 220' function as cathode and the conducting elements, ie. electrodes, 220 function as anode. The sample chamber 210 possesses a frame part 230 having input units 260 and withdrawal units 270 that are equipped with filters. The input and withdrawal units 260, 270 are so fitted into connector-type non-conducting elements 280 of the frame part 230 that the sample carrier 200 can be filled and emptied. In order to permit spectrophotometric or luminometric measurements to be carried out, as the case may be, the device 200 possesses optical units 290 between nonconducting areas 295 and 280 of the frame part 230, so that the optical units may be adapted in such a way that connections result. The connectors 225 of the electrodes 220, 220' may be used for electrical detection. It is also shown that random sequences 300 of the DNA mixture employed according to the invention are immobilised at the electrodes 220. It may also be provided for the random sequences 300 to be additionally, or exclusively, attached to the non-conducting element 240 in the region of the electrodes 220, 220'. In order to be able to carry out all process steps, that is sample dissociation, nucleic acid purification and as the case may be, nucleic acid washing as well as detection, with the sample carrier 200 while employing electric fields, one or more corresponding voltage-producing apparatuses must be connected to the sample carrier 200 so as to create the different electric fields required. The device according to the invention is therefore particularly characterised in that parts or regions of the sample chamber 210, in other words the wall, the bottom and/or the lid part are made up of electrodes capable of producing at least one electric field in the chamber, whereas openings may be present in walls, bottom or lid for sample removal, insertion and/or detection.

The procedure according to the invention using the aforementioned device initially provides for inserting a sample, such as *E. coli* cells present in water, into the sample carrier 200. Subsequently one may provide, as the case may be, for dielectrophoresis amid deployment of an electric field for concentrating respectively separating certain biological cells or as a precondition for an electro-fusion, whereby a corresponding voltage is fed to the connectors 225 of the electrodes 220, 220'. Here one may provide for an electro-fusion to boost the electrolysis or to carry out marking. Subsequently a voltage, for example in order to create pulsed electric fields or an electric field of constant voltage, is applied in such a way that there occurs an electrolysis of the biological cells or the viruses, with the parameters so chosen, as the case may be, that only certain biological cells are electrolysed. In the present example an electric field having a field strength of 0.5 kV/cm to 50 kV/cm is employed. Subsequently the conditions are so chosen that the nucleic acids released from the dissociated cells can, amid deployment of an electric field, electro-hybridise with either random sequences of the DNA mixture according to the invention that are freely present in the sample chamber or with the random sequences 300 of the DNA mixture employed according to the invention that have been immobilised on conducting or non-conducting regions of the sample chamber 210 in the anode area. Pulse counts of 1000 to 10000, a pulse duration respectively time constant of 2 $\mu$s to 50 ms, and field strengths of 0.5 kV/cm to 20 kV/cm were used for cell dissociation and electro-hybridisation.

Subsequently, electro-stringent washing may be carried out, as the case may be, amid pole reversal and concentration respectively depletion of certain nucleic acids and removal of undesired materials such as for example amplification inhibitors. As the case may be, an electro-elution and, as required, an amplification of the nucleic acids still remaining subsequently takes place in the sample chamber 210, preferably by way of an electrical, isothermic PCR as described in WO 97/47767. Finally, detection of the bound or freely present purified nucleic acids may take place, preferably electrically (described for example in Hintsche, 1999, cited elsewhere).

The expert will realise that between or after individually described steps—depending on the isolation strategy washing or elution of desired or, as the case may be, undesirable, substances or nucleic acids may take place, as well as an alteration in the electric field as far as polarity, field strength, pulse count, pulse length or pulse frequency.

EXAMPLE 6

FIG. 6 shows a device 400 according to the invention for carrying out a procedure according to the invention, with the device 400 consisting of a planar-shaped non-conducting frame. part 560 and at least two electrodes 500 integrated into this planar-shaped frame part 560. The device according to the invention 400 is constructed as a chip, that is, it does not possess a sample chamber formed by wall or lid parts. The invention thus also relates to a planar-shaped sample carrier, ie. a chip, consisting of a non-conducting chip base 560, also described as frame part, and two planar electrodes 500 integrated into this chip base 560. In a preferred manner nucleic acid-affine materials 550 such as for example a DNA mixture consisting of random sequences may be immobilised on the electrodes 500.

The procedure according to the invention is capable of being carried out in a chronological sequence by way of purposefully addressing the electrodes, for example electrode addressing mode 1 for the electrical dissociation of the biotic respectively abiotic material (isolation of nucleic acid), an electrode addressing mode 2 for the electrical purification of nucleic acid, an electrode addressing mode 3 for the electrical isothermic amplification of nucleic acid and an electrode addressing mode 4 for electric detection.

What is claimed is:

1. Procedure for isolating nucleic acids from a sample selected from the group consisting of procaryotic cells, eucaryotic cells, viruses, cell organelles, cell nuclei and liposomes comprising:

(a) dissociating the sample by application thereto of at least one electric field, so as to release the nucleic acids from the sample;

(b) bringing the released nucleic acids into contact with a material capable of binding nucleic acids under binding conditions; and (c) separating the bound nucleic acids from the remainder of the sample.

2. Procedure according to claim 1, wherein a pulsed electric field is applied to the sample.

3. Procedure according to claim 1, wherein an electric field having a constant voltage is applied to the sample.

4. Procedure according to claim 1, wherein at least two electric fields are applied to the sample.

5. Procedure according to claim 1, wherein said at least one electric field is applied while the nucleic acids are brought into contact with the material capable of binding nucleic acids.

6. Procedure according to claim 5, wherein a pulsed electric field is applied to the sample.

7. Procedure according to claim 5, wherein an electric field having a constant voltage is applied to the sample.

8. Procedure according to claim 1, wherein the polarity of the electric field is reversed while the nucleic acids are brought into contact with the material capable of binding nucleic acids.

9. Procedure according to claim 8, wherein the bound nucleic acids are washed during application of an electric field.

10. Procedure according to claim 1, comprising detecting the nucleic acids after the time at which they are bound to the material capable of binding nucleic acids.

11. Procedure according to claim 10, wherein the nucleic acids are separated from the material capable of binding nucleic acids prior to the detection.

12. Procedure according to claim 1, comprising amplifying the nucleic acids prior to the detection.

13. Procedure according to claim 1, wherein the material capable of binding nucleic acids is present in solution.

14. Procedure according to claim 1, wherein the material capable of binding nucleic acids is immobilised on a sample carrier.

15. Procedure according to claim 1, wherein the material capable of binding nucleic acids is selected from the group consisting of an anion exchanger, silica, diatoms, a nucleic acid-linking protein and a nucleic acid.

16. Procedure according to claim 1, wherein the material capable of binding nucleic acids is selected from the group consisting of a fragmented target genome, a mixture of random nucleic acid sequences and a sequence-specific nucleic acids sequence.

17. Procedure according to claim 16, wherein the nucleic acid sequence is an oligonucleotide.

* * * * *